US006194618B1

(12) United States Patent
Okawa

(10) Patent No.: US 6,194,618 B1
(45) Date of Patent: Feb. 27, 2001

(54) METHOD OF PRODUCING ISOBUTYLENE GLYCOL

(75) Inventor: Takashi Okawa, Niigata-ken (JP)

(73) Assignee: Mitsubishi Gas Chemical Company, Inc., Tokyo (JP)

(*) Notice: Subject to any disclaimer, the term of this patent is extended or adjusted under 35 U.S.C. 154(b) by 0 days.

(21) Appl. No.: 09/464,195

(22) Filed: Dec. 16, 1999

(30) Foreign Application Priority Data

Dec. 16, 1998 (JP) .................................................. 10-357811

(51) Int. Cl.$^7$ .................................................. C07C 29/149
(52) U.S. Cl. .................................................. 568/864
(58) Field of Search .................................................. 568/864

(56) References Cited

U.S. PATENT DOCUMENTS 2,094,611   10/1937   Lazier .................................. 260/156.5

FOREIGN PATENT DOCUMENTS

| 53-12804 | 2/1978 | (JP) . |
| 53-65807 | 6/1978 | (JP) . |
| 58-144331 | 8/1983 | (JP) . |
| 59-95226 | 6/1984 | (JP) . |

OTHER PUBLICATIONS

H. Adkins, et al., "The hydrogenation of esters to alcohols at 25–150 degrees", Journal of the American Chemical Society, vol. 70, 1948, pp. 3121–3125.

*Primary Examiner*—Peter O'Sullivan
(74) *Attorney, Agent, or Firm*—Antonelli, Terry, Stout & Kraus, LLP

(57) ABSTRACT

Isobutylene glycol is produced with a high yield by catalytically reducing methyl hydroxyisobutyrate in the presence of a catalyst containing at least one of copper and ruthenium. The reduction of methyl hydroxyisobutyrate in the presence of the specific catalyst involves selective reduction of only ester group.

13 Claims, No Drawings

METHOD OF PRODUCING ISOBUTYLENE GLYCOL

FIELD OF THE INVENTION

The present invention relates to a method of producing isobutylene glycol by catalytic reduction of methyl hydroxyisobutyrate. Isobutylene glycol is a useful compound as a raw material for producing polyester resins, polyester plasticizers, lubricating oils, polyester films and polyurethane resins; a solvent; a constitutional component of a developer, a shampoo, a perfume composition and an aqueous composition for unwrinkling fibrous products.

BACKGROUND OF THE INVENTION

There have been various proposals on the method of producing isobutylene glycol. For example, Japanese Patent Application Laid-Open No. 53-12804 discloses a method of producing isobutylene chlorohydrin and isobutylene glycol by reacting isobutene with oxygen-containing gas in an aqueous solution containing halide ion in the presence of a compound or ion of an element selected from the group consisting of tin, tellurium, iridium and titanium. Japanese Patent Application Laid-Open No. 53-65807 discloses a liquid phase oxidation of isobutene in an aqueous solvent in the presence of a catalyst. Japanese Patent Application Laid-Open No. 58-144331 discloses a method of producing a vicinal glycol by irradiating methanol with light in the presence of acetone. Japanese Patent Application Laid-Open No. 59-95226 discloses a method of producing diols by hydrogenation of acetone cyanohydrin in a water-containing medium, comprising a fist step of hydrogenating acetone cyanohydrin until one mol of hydrogen is absorbed per one mol of acetone cyanohydrin at −20 to 20° C. under a hydrogen pressure of 10 bar or lower in the presence of a palladium or platinum catalyst and an acid in an amount equivalent to acetone cyanohydrin or more, or in the presence of metallic nickel and an acid in an amount equivalent to acetone cyanohydrin or more, and a second step of hydrogenating acetone cyanohydrin at 30 to 100° C. under a hydrogen pressure of 10 to 150 bar in the presence of metallic nickel.

However, the above methods have problems in putting them into industrial application. For example, in the oxidation of isobutene with oxygen in the presence of hydrogen bromide and tellurium oxide catalyst described in Japanese Patent Application Laid-Open No. 53-12804, isobutylene chlorohydrin is produced 2.6 times as much as isobutylene glycol, thereby resulting in a disadvantageously low yield of isobutylene glycol. In the air oxidation of isobutylene in water solvent in the presence of potassium dichromate described in Japanese Patent Application Laid-Open No. 53-65807, the rate of reaction is low and the yield of isobutylene glycol is unfavorably as low as 38%. In the method taught by Japanese Patent Application Laid-Open No. 58-144331, methanol and acetone in a pyrex reactor are irradiated with light from a high pressure mercury lamp. This method has defects of low rate of reaction and low selectivity to isobutylene glycol due to by-production of ethylene glycol and pinacol. Although the method taught by Japanese Patent Application Laid-Open No. 59-95226 provides a yield of isobutylene glycol relatively as high as 81%, it requires rather complicated reaction operations for industrial use.

SUMMARY OF THE INVENTION

In view of the above problems, an object of the present invention is to provide an industrially advantageous method of producing isobutylene glycol.

As a result of intensive research for solving the above problems, the inventor has found that only the ester group of two functional groups, ester group and hydroxyl group, in methyl hydroxyisobutyrate molecule is selectively hydrogenated by the catalytic reduction using a specific catalyst, thereby to produce isobutylene glycol in a high yield. The selective reduction of the ester group of methyl hydroxyisobutyrate is not known in the art. The present invention has been accomplished based on this finding.

Thus, the present invention provides a method of producing isobutylene glycol comprising a step of catalytically reducing methyl hydroxyisobutyrate in the presence of a catalyst containing at least one of copper component and ruthenium component.

DETAILED DESCRIPTION OF THE INVENTION

The present invention will be described below in detail.

Methyl hydroxyisobutyrate used in the present invention as the starting material may be produced by several methods. For example, methyl hydroxyisobutyrate may be produced from acetone and methanol as raw materials. Acetone is reacted with hydrogen cyanide to produce acetone cyanohydrin (first step), followed by amidation of acetone cyanohydrin to hydroxyisobutyramide in the present of a manganese catalyst, etc. (second step). Hydroxyisobutyramide is then reacted with methyl formate in the presence of an alkali catalyst, etc. to obtain methyl hydroxyisobutyrate and formamide (third step). The by-produced formamide undergoes pyrolysis in the presence of an iron catalyst, etc. to regenerate hydrogen cyanide (fourth step), which is recycled to the first step. Methyl formate is easily produced by dehydrogenating methanol in the presence of a copper catalyst, etc. (fifth step). Thus, methyl hydroxyisobutyrate is produced at relatively low cost using easily available acetone and methanol as raw materials.

Since methyl hydroxyisobutyrate is converted to methyl methacrylate (MMA) by dehydration in the presence of a zeolite catalyst, etc. (sixth step), MMA has recently come to be industrially produced by a process comprising the first to sixth steps mentioned above. Such a process for manufacturing MMA is characterized by the use of acetone and methanol as main raw materials and the by-production of no ammonium sulfate. The intermediary methyl hydroxyisobutyrate in the MMA manufacturing process may be effectively utilized in the present invention.

The catalytic reduction of methyl hydroxyisobutyrate is exothermic, and usually carried out in a solvent so as to suitably control the temperature rise due to reaction heats or to increase the reaction rate. Although, the solvent usable in the present invention may include an inert solvent selected from aliphatic hydrocarbons such as n-hexane, n-heptane and n-octane; aromatic hydrocarbons such as benzene, toluene, and xylene; alicyclic hydrocarbons such as cyclohexane; and ethers such as 1,4-dioxane and tetrahydrofuran, isobutylene glycol and/or methanol are preferably used as the solvent because the step for recovering the solvent from the liquid reaction mixture and the step for recycling the recovered solvent can be omitted. The solvent is used in an amount so that the concentration of methyl hydroxyisobutyrate in starting mixture is 1 to 50% by weight, preferably 5 to 30% by weight. An amount of the solvent resulting in a concentration lower than the above range decreases the space time yield, while an amount resulting in a concentration higher than the above range makes the temperature control of the reaction zone difficult.

Hydrogen gas of technical grade is sufficient for use in the present invention. For example, a mixed gas of hydrogen and an inert gas such as nitrogen, carbon dioxide and methane is usable. The hydrogen content of the mixed gas is preferably 50 mol % or more. The amount of hydrogen to be used is 2 to 50 mol per one mol of methyl hydroxyisobutyrate. When less than the above range, the amount of methyl hydroxyisobutyrate remaining unreacted is increased, while an amount exceeding the above range is of poor economy because a great amount of hydrogen gas circulates as unreacted.

The catalyst used in the present invention contains at least one of copper component and ruthenium component. A copper base catalyst is preferably a catalyst modified by zinc component and/or chromium component such as a copper-zinc catalyst, a copper-chromium catalyst and a copper-zinc-chromium catalyst. The copper base catalyst may be used directly or may be supported on a carrier such as activated carbon, alumina, silica and diatomaceous earth. The copper base catalyst preferably comprises, assuming that the metal components are all in oxide forms, 20 to 60% by weight of copper oxide, 0 to 70% by weight of zinc oxide, 0 to 70% by weight of chromium oxide and 0 to 60% by weight of the carrier. The copper base catalyst may further contain, if desired, another metal component such as zirconium component, manganese component and barium component in an amount of 0 to 50% by weight for zirconium component, 0 to 5% by weight for manganese component and 0 to 10% by weight for barium component, each in terms of metal oxide. The copper base catalyst may be in the form of powder, or may be compacted or extruded into a cylindrical form.

A ruthenium base catalyst is generally supported on a carrier such as activated carbon, alumina, silica and diatomaceous earth. The supported amount of ruthenium component (metal basis) is 0.1 to 10% by weight, preferably 0.5 to 5% by weight based on the catalyst. The ruthenium base catalyst may further contain, if desired, another metal component such as zinc component, chromium component, manganese component and barium component in an amount of 0 to 5% by weight for zinc component, 0 to 5% by weight for chromium component, 0 to 1% by weight for manganese component and 0 to 1% by weight for barium component, each in terms of metal oxide. The ruthenium base catalyst may be in the form of powder, or may be shaped into spherical or cylindrical form by compacting or extruding.

Each metal component of the copper base or ruthenium base catalyst may be in metallic form or oxide form, preferably in metallic form, and up to about 10% by mol of each metal component may be in the oxide form without adversely affecting the effect of the present invention. Generally, prior to the use in the catalytic reduction, it is preferred to subject the copper base or ruthenium base catalyst to reduction treatment, for example, in the manner described below.

The amount of the catalyst used in the catalytic reduction is preferably 0.01 to 1 g (metal oxide basis) per one gram of methyl hydroxyisobutyrate.

The catalytic reduction of the present invention may be carried out as a liquid phase suspension reaction or a fixed bed reaction either in batch-wise manner or continuous manner, and the fixed bed reaction is industrially preferred because the separation of the catalyst from the liquid reaction mixture is not needed. In the fixed bed reaction, a shell and tube reactor may be used to remove the reaction heats through heating medium. However, since this reactor makes the overall shape of the apparatus more complicated to increase the fixed cost, an insulated reactor is generally used.

The starting liquid and hydrogen gas are introduced into the reactor from the top or bottom thereof. The introduced starting liquid and hydrogen gas flow through the reactor downwardly or upwardly while forming vapor-liquid parallel flows, and pass through a catalyst packed area. The liquid reaction mixture and hydrogen gas after contacting the catalyst are taken out from the bottom or top of the reactor.

The reaction temperature is 70 to 250° C., preferably 120 to 200° C. Temperature lower than the above range is impractical because the rate of reaction is lowered. When higher than the above range, the yield is poor due to increased side reactions. The reaction pressure is 5 to 200 kgf/cm$^2$, preferably 20 to 100 kgf/cm$^2$. Pressure less than 5 kgf/cm$^2$ is impractical due to a small rate of reaction. Since the rate of reaction is not so increased, pressure higher than 200 kgf/cm$^2$ is less economical.

In a continuous fixed bed reaction, it is preferred to feed the starting liquid to the reactor in a rate as high as possible according to the rate of reaction determined by the reaction conditions while regulating the unreacted amount in the liquid reaction mixture within allowable level. Although not strictly specified, the feed rate is usually 0.25 to 10 hr$^{-1}$ in terms of liquid hourly space velocity (LHSV) representing a feed rate by volume of the starting liquid per one hour and per unit volume of the packed catalyst. Also, although not strictly specified because the rate of reaction depends on the reaction conditions, the reaction time of a batch-wise liquid phase suspension reaction is usually 0.1 to 4 hours.

The liquid reaction mixture obtained in the present invention contains isobutylene glycol, solvent, and in some cases, a small amount of unreacted methyl hydroxyisobutyrate, by-products, etc. Isobutylene glycol is easily separated from the liquid reaction mixture in a high purity by known batchwise or continuous distillation techniques under ordinary pressure or reduced pressure.

The present invention will be described in further detail by way of the following Examples and Comparative Examples. However, it should be noted that the scope of the present invention is not limited to the following Examples.

In the Examples and Comparative Examples, the copper base catalyst and the nickel base catalyst were subjected to reduction treatment prior to use in respective reactions.

Reduction Treatment

A quartz tube (internal diameter: 8 mm, length: 80 cm) packed with 2 g of powdery catalyst was placed in a heating electric furnace. Then, the temperature of the catalyst layer was raised to 140° C. while passing nitrogen gas through the tube at a flow rate of 30 ml/min. The nitrogen gas was gradually changed to hydrogen gas while maintaining the temperature at 140° C, and finally, the catalyst was heat-treated for 4 hours while passing hydrogen gas through the tube at a flow rate of 30 ml/min. Then, after gradually raising the temperature of the catalyst layer to 240° C., the catalyst was further heat-treated for 3 hours while maintaining the temperature and the flow rate of hydrogen gas at 240° C. and 30 ml/min. After the reduction treatment is completed, the catalyst in the quartz tube was cooled to room temperature while passing hydrogen gas therethrough. The catalyst thus treated was stored in an autoclave purged in advance with nitrogen gas until used in the reaction.

EXAMPLE 1

After replacing the atmosphere of a 100 ml stainless shaking autoclave with nitrogen gas, were sealed into the autoclave 5 g of methyl hydroxyisobutyrate, 10 g of methanol, and a catalyst obtained by reducing 2 g of powdery Cu—Cr—Mn catalyst (CuO: 44.8% by weight; $Cr_2O_3$:43.8% by weight; $Mn_2O_3$:4.1% by weight; and balance comprising crystallization water, etc.) in the manner described above. The internal pressure of the autoclave was adjusted to 100 kgf/cm$^2$ by introducing hydrogen gas (purity: 99% or more). Then, the autoclave was placed in an electric furnace on a shaker. After the internal temperature reached 140° C., the reaction was allowed to proceed under shaking for 2 hours while maintaining the temperature at 140° C.

After the reaction was completed, the autoclave was cooled and the gas therein was released. The content in the autoclave was filtered through a glass filter to separate the content into the catalyst and mother liquor. Compositional analysis was made on the mother liquor by internal standard gas chromatography. The results showed that the conversion of methyl hydroxyisobutyrate was 99.7% and the selectivity to isobutylene glycol was 96.3%. The percentage for the conversion and the selectivity referred to herein are expressed by molar basis.

Thereafter, the recovered catalyst, 5 g of methyl hydroxyisobutyrate and 10 g of methanol were sealed in the same autoclave purged in advance with nitrogen gas. The internal pressure of the autoclave was adjusted to 100 kgf/cm$^2$ by introducing hydrogen gas. Then, the autoclave was placed in an electric furnace on a shaker. After the internal temperature reached 140° C., the reaction was allowed to proceed under shaking for 2 hours while maintaining the temperature at 140° C.

After the reaction was completed, the autoclave was cooled and the gas was released. Compositional analysis was made on the liquid reaction mixture taken out of the autoclave by internal standard gas chromatography. The results showed that the conversion of methyl hydroxyisobutyrate was 99.8% and the selectivity to isobutylene glycol was 97.1%.

EXAMPLE 2

In the same manner as in Example 1, 5 g of methyl hydroxyisobutyrate, 10 g of isobutylene glycol and a catalyst prepared by reducing 2 g of Cu—Cr—Mn catalyst in the same manner as in Example 1 were sealed in an autoclave. The internal pressure of the autoclave was adjusted to 100 kgf/cm$^2$ by introducing hydrogen gas. Then, the autoclave was placed in an electric furnace on a shaker. After the internal temperature reached 160° C., the reaction was allowed to proceed under shaking for 1 hour while maintaining the temperature at 160° C.

After the reaction was completed, the autoclave was cooled and the gas therein was released. Compositional analysis was made on the liquid reaction mixture taken out of the autoclave by internal standard gas chromatography. The results showed that the conversion of methyl hydroxyisobutyrate was 99.9% and the selectivity to isobutylene glycol was 93.9%.

EXAMPLE 3

In the same manner as in Example 1, 5 g of methyl hydroxyisobutyrate, 10 g of methanol and a catalyst prepared by reducing 2 g of Cu—Zn—Zr catalyst (CuO: 37.6% by weight; ZnO: 7.5% by weight; ZrO: 40.5% by weight; balance comprising crystallization water, etc.) in the same manner as in Example 1 were sealed in an autoclave. The internal pressure of the autoclave was adjusted to 100 kgf/cm$^2$ by introducing hydrogen gas. Then, the autoclave was placed in an electric furnace on a shaker. After the internal temperature reached 160° C., the reaction was allowed to proceed under shaking for 1 hour while maintaining the temperature at 160° C.

After the reaction was completed, the autoclave was cooled and the gas therein was released. Compositional analysis was made on the liquid reaction mixture taken out of the autoclave by internal standard gas chromatography. The results showed that the conversion of methyl hydroxyisobutyrate was 99.9% and the selectivity to isobutylene glycol was 92.5%.

EXAMPLE 4

The procedures of Example 3 were repeated except for adjusting the internal pressure to 50 kgf/cm$^2$. After the reaction was completed, the autoclave was cooled and the gas therein was released. Compositional analysis was made on the liquid reaction mixture taken out of the autoclave by internal standard gas chromatography. The results showed that the conversion of methyl hydroxyisobutyrate was 99.8% and the selectivity to isobutylene glycol was 83.2%.

EXAMPLE 5

The procedures of Example 2 were repeated except for using a catalyst obtained by reducing 2 g of Cu—Cr—Mn—Ba catalyst (CuO: 43.5% by weight; $Cr_2O_3$:42.5% by weight; $Mn_2O_3$:2.3% by weight; BaO: 2.5% by weight; and balance comprising crystallization water, etc.). The conversion of methyl hydroxyisobutyrate was 98.4% and the selectivity to isobutylene glycol was 83.2%.

EXAMPLE 6

The procedures of Example 3 were repeated except for using 5% ruthenium/carbon powder as a catalyst. The conversion of methyl hydroxyisobutyrate was 58.7% and the selectivity to isobutylene glycol was 71.6%.

EXAMPLE 7

Into a fixed bed isothermal reactor with 25 mm internal diameter and 1 m length, 400 ml of a cylindrically shaped Cu—Cr—Mn catalyst (CuO: 36.5% by weight; $Cr_2O_3$:45.5% by weight; $Mn_2O_3$:3.4% by weight; and balance crystallization water, etc.).

Reduction Treatment

After replacing the atmosphere of the reactor with nitrogen gas, the temperature of the catalyst layer was raised to 110° C. at a temperature elevation rate of 20° C./hr while passing nitrogen gas through the reactor at a space velocity (SV) of 200 hr$^{-1}$. "SV" represents a feed rate by volume of the gas per one hour and per unit volume of the packed catalyst. Then, while passing a mixed nitrogen gas containing 5% hydrogen through the reactor, the temperature of the catalyst layer was raised to 140° C. at a temperature elevation rate of 10°C./hr. Thereafter the mixed gas was continued to flow, and after the temperature rise of the catalyst layer was ceased and the formation of water due to reduction became not noticed, the mixed gas was changed to hydrogen gas by gradually increasing the hydrogen content. Then, the feed rate of hydrogen gas was increased to SV of 300 hr$^{-1}$, and the temperature of the catalyst layer was raised to 200° C. at a temperature elevation rate of 10°C./hr. The flow of hydrogen gas was continued for 5 hours while maintaining the temperature and the feed rate at 200° C. and 300 hr$^1$ to complete the reduction treatment.

Hydrogenation of Methyl Hydroxyisobutyrate

The reaction pressure was adjusted to 100 kg/cm$^2$ by introducing hydrogen gas from the top of the reactor via a pressure regulator, and the temperature of the catalyst layer was maintained at 160° C. A liquid mixture consisting of 30 parts by weight of methyl hydroxyisobutyrate and 70 parts by weight of methanol was introduced from the top of the reactor at a feed rate of 200 ml/hr, thereby permitting the hydrogenation reaction to proceed. The effluent from the bottom of the reactor was separated into liquid and gas, and the gas was released at a flow rate of 120 ml/hr. After the reaction reached a steady state, a liquid reaction mixture was sampled for compositional analysis by internal standard gas chromatography.

The results showed that the conversion of methyl hydroxyisobutyrate was 99.8% and the selectivity to isobutylene glycol was 97.2%.

Isolation of Isobutylene Glycol

By distilling away methanol using a rotary evaporator, 235 g of crude isobutylene glycol was obtained from 1 kg of liquid reaction mixture. The crude product was subjected to batch distillation (pressure: 11 mm Hg; reflux ratio: 5) using a packed column (theoretical plates: 14). The fractions at a distillation rate of 8 to 92% (distillation temperature: 78 to 79° C.) were collected to obtain a main distillate. The results of gas chromatographic compositional analysis of the main distillate showed that the distillate was isobutylene glycol with 99.9% or more purity.

COMPARATIVE EXAMPLE 1

The procedures of Example 3 were repeated except for using a catalyst prepared by reducing a nickel-diatomaceous earth (Ni: 58%).

The formation of isobutylene glycol was not detected.

COMPARATIVE EXAMPLE 2

The procedures of Example 3 were repeated except for using 5% palladium/carbon powder as a catalyst.

The formation of isobutylene glycol was not detected.

As described above, of the ester group and the hydroxyl group in methyl hydroxyisobutyrate molecule, only the ester group is selectively and catalytically reduced to produce isobutylene glycol in a high yield. The present invention is of great significance in industrially producing isobutylene glycol.

What is claimed is:

1. A method of producing isobutylene glycol comprising a step of catalytically reducing methyl hydroxyisobutyrate in the presence of a catalyst containing at least one of a copper component and a ruthenium component.

2. The method of producing isobutylene glycol according to claim 1, wherein the catalyst is a copper base catalyst modified by a zinc component and/or a chromium component.

3. The method of producing isobutylene glycol according to claim 2, wherein the catalyst further comprises at least one metal component selected from the group consisting of a zirconium component, a manganese component and a barium component.

4. The method of producing isobutylene glycol according to claim 2, wherein the catalyst comprising 20 to 60% by weight of the copper component and at least one of the zinc component and the chromium component each in an amount up to 70% by weight excluding zero, said weight percentages being based on a total weight of the catalyst and expressed on oxide basis.

5. The method of producing isobutylene glycol according to claim 4, wherein the catalyst further comprising at least one metal component selected from the group consisting of a zirconium component, a manganese component and a barium component in an amount up to 50% by weight excluding zero for the zirconium component, up to 5% by weight excluding zero for the manganese component and up to 10% by weight excluding zero for the barium component, said weight percentages being based on a total weight of the catalyst and expressed on oxide basis.

6. The method of producing isobutylene glycol according to claim 1, wherein the catalyst is a ruthenium base catalyst.

7. The method of producing isobutylene glycol according to claim 6, wherein the ruthenium base catalyst comprises a ruthenium component supported on a carrier selected from the group consisting of activated carbon, alumina, silica and diatomaceous earth, said ruthenium component being supported in an amount of 0.1 to 10% by weight, in terms of metal, based on the catalyst.

8. The method of producing isobutylene glycol according to claim 7, wherein the ruthenium base catalyst further comprises at least one metal component selected from the group consisting of a zinc component, a chromium component, a manganese component and a barium component.

9. The method of producing isobutylene glycol according to claim 1, wherein methyl hydroxyisobutyrate is catalytically reduced in methanol, isobutylene glycol or a mixture thereof.

10. The method of producing isobutylene glycol according to claim 1, wherein methyl hydroxyisobutyrate is catalytically reduced at 70 to 250° C.

11. The method of producing isobutylene glycol according to claim 1, wherein methyl hydroxyisobutyrate is catalytically reduced under a pressure of 5 to 200 kgf/cm$^2$.

12. A method of producing isobutylene glycol in a continuous manner, which comprises catalytically reducing methyl hydroxyisobutyrate in a reactor with hydrogen gas in the presence of a catalyst containing at least one of a copper component and a ruthenium component at a temperature of 70 to 250° C. under a pressure of 5 to 200 kgf/cm$^2$, said hydrogen gas being introduced into the reactor in a flow rate so as to maintain an internal pressure of the reactor within the above pressure range while simultaneously feeding a starting liquid containing at least methyl hydroxyisobutyrate into the reactor at a liquid hourly space velocity of 0.25 to 10 hr$^{-1}$.

13. A method of producing isobutylene glycol in a batchwise manner, which comprises catalytically reducing methyl hydroxyisobutyrate with hydrogen gas in the presence of a catalyst containing at least one of a copper component and a ruthenium component at a temperature of 70 to 250° C. under a pressure of 5 to 200 kgf/cm$^2$ for 0.1 to 4 hours.

* * * * *